US009512054B2

(12) United States Patent
Johnson et al.

(10) Patent No.: US 9,512,054 B2
(45) Date of Patent: Dec. 6, 2016

(54) METHOD FOR MAKING A HIGH PURITY ALCOHOL

(71) Applicant: Eastman Chemical Company, Kingsport, TN (US)

(72) Inventors: Chad A. Johnson, Longview, TX (US); Xianchun Wu, Longview, TX (US); Kenneth Wayne Hampton, Jr., Gilmer, TX (US); Raymond Prescott Cottle, Longview, TX (US); Eugene H. Brown, Gilmer, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/618,436

(22) Filed: Feb. 10, 2015

(65) Prior Publication Data

US 2016/0229776 A1  Aug. 11, 2016

(51) Int. Cl.
| | |
|---|---|
| *C07C 41/44* | (2006.01) |
| *C07C 41/42* | (2006.01) |
| *C07C 43/13* | (2006.01) |
| *B01J 23/46* | (2006.01) |
| *B01J 23/755* | (2006.01) |

(52) U.S. Cl.
CPC ............. *C07C 41/44* (2013.01); *B01J 23/462* (2013.01); *B01J 23/755* (2013.01); *C07C 41/42* (2013.01); *C07C 43/13* (2013.01)

(58) Field of Classification Search
CPC .......... C07C 41/44; C07C 41/42; C07C 43/13; B01J 23/462; B01J 23/755
See application file for complete search history.

(56) References Cited

U.S. PATENT DOCUMENTS

| | | | |
|---|---|---|---|
| 5,684,215 | A | 11/1997 | Horn et al. |
| 5,902,916 | A | 5/1999 | Rühl et al. |
| 6,117,277 | A | 9/2000 | Zgorzelski et al. |
| 6,156,933 | A | 12/2000 | Poliakoff et al. |
| 6,207,865 | B1 | 3/2001 | Breitscheidel et al. |
| 6,391,284 | B1 | 5/2002 | Gangarosa, Sr. |
| 6,441,255 | B1 | 8/2002 | Haas et al. |
| 6,448,457 | B1 | 9/2002 | Hesse et al. |
| 6,455,743 | B1 | 9/2002 | Ueda et al. |
| 6,600,078 | B1 | 7/2003 | Mahmud et al. |
| 6,756,028 | B2 | 6/2004 | Korl et al. |
| 6,765,119 | B2 | 7/2004 | Hoffmann et al. |
| 6,916,964 | B2 | 7/2005 | Göbbel et al. |
| 7,084,312 | B1 | 8/2006 | Huber et al. |
| 7,232,934 | B2 | 6/2007 | Saleh et al. |
| 7,358,404 | B2 | 4/2008 | Kawasaki et al. |
| 7,459,571 | B2 | 12/2008 | Schlitter et al. |
| 7,479,576 | B1 | 1/2009 | Hassan et al. |
| 7,498,450 | B2 | 3/2009 | Wood et al. |
| 7,700,814 | B2 | 4/2010 | Garton et al. |
| 7,790,938 | B2 | 9/2010 | Kawasaki et al. |
| 7,875,742 | B2 | 1/2011 | Soled et al. |
| 7,914,745 | B2 | 3/2011 | Hassan et al. |
| 8,168,836 | B2 | 5/2012 | Hassan et al. |
| 8,288,596 | B2 | 10/2012 | Garton et al. |
| 8,378,155 | B2 | 2/2013 | Hassan et al. |
| 2013/0237726 | A1 | 9/2013 | Krokoszinski et al. |

FOREIGN PATENT DOCUMENTS

CA          507744       * 11/1954

OTHER PUBLICATIONS

Malherbe et al., "Highly Selective synthesis of 2-butoxy ethanol over Mg/Al/V mixed oxide catalysts derived from hydrotalcites," Catalysis Letters, 67 (2000) 197-202.*

* cited by examiner

*Primary Examiner* — Paul A. Zucker
*Assistant Examiner* — Mark Luderer
(74) *Attorney, Agent, or Firm* — Matthew W. Smith

(57) ABSTRACT

There is provided is a method for making a higher purity alcohol comprising: a) contacting an impure alcohol composition comprising: (i) an alcohol compound; and (ii) from about 50 ppm to about 5 weight percent, based on the weight of the impure alcohol composition, of at least one hydrogenable contaminant having an unsaturated bond, with hydrogen in a hydrogenation reactor and in the presence of a hydrogenation catalyst to produce a reaction mixture comprising the alcohol compound and a hydrogenated contaminant product wherein at least 10 mole % of the at least one hydrogenable contaminant in the reaction mixture is converted; and b) separating the alcohol compound from at least a portion of the reaction mixture to produce an enriched alcohol composition having a lower concentration of the hydrogenated contaminant product. There is also provided an alcohol composition having less than about 500 ppm of at least one hydrogenable contaminant.

20 Claims, No Drawings

METHOD FOR MAKING A HIGH PURITY ALCOHOL

BACKGROUND OF THE INVENTION

1. Field of the Invention

The present invention relates to a method for making a high purity alcohol and more particularly to a method for making high purity ethylene glycol monoethers having ultra-low concentrations of reactive unsaturated impurities, such as aldehydes, enals and enols.

2. Description of the Prior Art

Ethylene glycol monobutyl ether or 2-butoxyethanol (EB) is a well-known commercialized product having many commercial and industrial uses. For example, 2-butoxyethanol is known to be utilized in surface coatings such as inks, paints and varnish, cleaning solvents, automotive fluid additives and electronics to name a few. U.S. consumption of 2-butoxyethanol over the past decade has averaged about 140 thousand metric tons and an average growth rate per year of about 2.6 percent.

The method of manufacture of such ethylene glycol monoethers is well known and published in various patents and publications known to those skilled in the art. Generally, the method for making the ethylene glycol monoethers is an addition chemical reaction and typically comprises the liquid-phase reaction of ethylene oxide with different molecular ratios of the appropriate anhydrous alcohol, such as methyl, ethyl or butyl alcohol, under various conditions of temperature, pressure and catalysts. In all three cases ethylene oxide can proceed to react further to produce the monoethers of diethylene glycol, triethylene glycol and higher glycols. To minimize and control the proportion of these higher molecular weight glycol ethers, an excess of the alcohol is fed to the reactor. Furthermore, depending upon the reaction conditions and impurities in the feedstocks and production process, chemical species having an unsaturated bond, such as an aldehyde, enal, or enol, may be produced. The desired glycol monoether is not formed as a pure compound in the reaction but must be separated from these unreacted raw materials, co-products, and impurities.

Typically, the separation is accomplished by distillation or rectification. These distillation columns generally have a plurality of plates or, if utilizing a packed column, theoretical stages. The excess alcohol feedstock is the removed as a low boiling fraction in the first distillation column. Then, the monoethers of diethylene glycol, triethylene glycol and higher glycols are removed as a high-boiling fraction in the following distillation columns. The product, ethylene glycol monoether, is recovered as a low boiling fraction from the second distillation column. The purity of the product glycol ether can be limited by a plurality of factors, such as, for example, economic and environmental incentive to maximize yield. Impurities can't be reduced by discarding a significant amount of the product glycol ether in the heavy fraction. Likewise, the unreacted alcohol stream is recycled to the reactor instead of being purged or discarded. Thermodynamic and mass transfer limitations inherent to one or more of the distillation columns and their designs also limit the purity of the desired product. Additionally, the boiling points of some impurities are too close to the product glycol ether for economic separation. Another consideration is high temperatures and/or residual oxygen in the distillation columns can initiate thermal or oxidative decomposition and generate additional impurities.

In the case of EB, even after distillation the product may contain up to 5 weight % of unsaturated impurities formed in the manufacturing process; such as n-butyraldehyde, enals such as 2-ethylhexenal, and enols such as 2-ethylhex-2-en-1-ol. These species are difficult to separate from the EB by conventional distillation. Moreover, in applications that require extremely high levels of cleaning and minimal residue, such as electronic or nanotechnology applications, these impurities may interfere with the performance characteristics of EB or even react with the substrate or other components in the cleaning mixture Accordingly, there is a need for an ethylene glycol monoether, and particularly 2-butoxyethanol product having a high purity, and a low to non-detectable concentration of contaminants having an unsaturated bond such as n-butyraldehyde, 2-ethylhexenal, and 2-ethylhex-2-en-1-ol.

SUMMARY OF THE INVENTION

There is now provide a method for making a high purity alcohol, and particularly a high purity ethylene glycol monoether including the steps of: a) contacting an impure alcohol feed comprising an alcohol compound and from about 50 ppm to about 5 weight %, based on the weight of the impure alcohol composition, of at least one hydrogenable contaminant having an unsaturated bond, with hydrogen in a hydrogenation reactor and in the presence of a hydrogenation catalyst to produce a reaction mixture comprising the alcohol compound and a hydrogenated contaminant product wherein at least 50 mole % of the hydrogenable contaminant in the reaction mixture is converted; and then b) separating the alcohol compound from at least a portion of the reaction mixture to produce an enriched alcohol composition having a lower concentration of the hydrogenated contaminant product.

There is also provided a method for making a higher purity alcohol comprising the steps of: a) contacting an impure alcohol composition comprising: an alcohol compound that is the reaction product from a primary alcohol reactant and an ethylene oxide reactant, and from about 200 ppm to about 5 weight percent, based on the weight of the impure alcohol composition, of at least one hydrogenable contaminant having an unsaturated bond with hydrogen in a hydrogenation reactor and in the presence of a hydrogenation catalyst to produce a reaction mixture comprising the alcohol compound and a hydrogenated contaminant product wherein at least 50 mole % of the at least one hydrogenable contaminant in said reaction mixture is converted; and b) separating the alcohol compound from at least a portion of the reaction mixture to produce an enriched alcohol composition a having lower concentration of the hydrogenated contaminant product.

The invention also provides for an alcohol composition comprising alcohols that are the reaction product from a primary alcohol reactant and an ethylene oxide reactant and having less than about 500 ppm of at least one hydrogenable contaminant comprising an aldehyde, an enal, an enol, and mixtures thereof.

The method of the invention desirably makes a higher purity alcohol product relative to its low purity alcohol feed. Desirably, the method also can make a high purity ethylene glycol monoether product, such as 2-butoxyethanol, relative to a low purity ethylene glycol monoether feed. Desirably, the method can also make a purified alcohol composition having a low concentration of at least one hydrogenable contaminant, and desirably less than 500 ppm of at least one hydrogenable contaminant.

DETAILED DESCRIPTION OF THE INVENTION

The method for making a higher purity alcohol comprises: a) contacting an impure alcohol composition comprising: (i) an alcohol compound; and (ii) from about 50 ppm to about 5 weight percent, based on the weight of the impure alcohol composition, of at least one hydrogenable contaminant having an unsaturated bond, with hydrogen in a hydrogenation reactor and in the presence of a hydrogenation catalyst to produce a reaction mixture comprising the alcohol compound and a hydrogenated contaminant product wherein at least 50 mole % of the at least one hydrogenable contaminant in the reaction mixture is converted; and b) separating the alcohol compound from at least a portion of the reaction mixture to produce an enriched alcohol composition having a lower concentration of the hydrogenated contaminant product.

The method for making a higher purity alcohol can also include: a) contacting an impure alcohol composition comprising: (i) an alcohol compound selected from alcohols that are the reaction product of a primary alcohol reactant and an ethylene oxide reactant; and (ii) from about 200 ppm to about 5 weight percent, based on the weight of the impure alcohol composition, of at least one hydrogenable contaminant having an unsaturated bond, with hydrogen in a hydrogenation reactor and in the presence of a hydrogenation catalyst to produce a reaction mixture comprising the alcohol compound and a hydrogenated contaminant product, wherein at least 50 mole % of the at least one hydrogenable contaminant in the reaction mixture is converted; and b) separating the alcohol compound from at least a portion of the reaction mixture to produce an enriched alcohol composition having a lower concentration of the hydrogenated contaminant product.

The low purity alcohol feed can be an ethylene glycol monoether selected from alcohols that are the reaction product from a primary alcohol reactant, such as methyl, ethyl and n-butyl alcohols, and an ethylene oxide reactant. Generally, the reaction product of the primary alcohol and ethylene oxide results in a product that comprises at least one hydrogenable contaminant having an unsaturated bond. As used herein, the term "hydrogenable" is used to describe a compound, mixture, or blend that includes a compound having at least one unsaturated bond that is susceptible to hydrogenation so that at least 10 mole percent of the compound is converted to a "hydrogenated" compound having at least one unsaturated bond converted to a saturated bond.

The low purity alcohol can be an ethylene glycol monoether selected from ethylene glycol monomethyl ether, ethylene glycol monoethyl ether and ethylene glycol monobutyl ether and mixtures thereof. The low purity alcohol feed can also be the reaction product from n-butyl alcohol and ethylene oxide, i.e., ethylene glycol monobutyl ether, or 2-butoxyethanol (EB). Although the following detailed description is directed toward ethylene glycol monobutyl ether one skilled in the art will understand that the method of the present invention is applicable to other ethylene glycol monoethers containing one or more hydrogenable, hydrogenable contaminants.

Generally, when making ethylene glycol monoethers several contaminants remain in the product due to the boiling points of the desired product and that of the contaminants, making separation very difficult. In the case where the ethylene glycol monoether is ethylene glycol monobutyl ether (boiling point 171.3° C.) the product may contain one or more of such hydrogenable impurities such as n-butryaldehyde (B.P. 75° C.), 2-ethylhexenal (B.P. 172° C.), and 2-ethylhex-2-en-1-ol (B.P. 196° C.). Initially, the crude product undergoes typical distillation in one or more distillation columns that may be under reduced pressure to assist in differentiating the boiling point differences to produce a low purity or impure product having from 500 parts per million (ppm) to about 5 weight %, based on the weight of the impure alcohol composition, of at least one hydrogenable contaminant, or from about 500 ppm to about 4 weight % of at least one hydrogenable contaminant, or from about 500 ppm to about 3 weight % of at least one hydrogenable contaminant, or from about 500 ppm to about 2 weight % of at least one hydrogenable contaminant, or from about 400 ppm to about 5 weight % of at least one hydrogenable contaminant, or from about 400 ppm to about 4 weight % of at least one hydrogenable contaminant, or from about 400 ppm to about 3 weight % of at least one hydrogenable contaminant, or from about 400 ppm to about 2 weight % of at least one hydrogenable contaminant, or from 300 to about 5 weight % of at least one hydrogenable contaminant, or from about 300 ppm to about 4 weight % of at least one hydrogenable contaminant, or from about 300 ppm to about 3 weight % of at least one hydrogenable contaminant, or from about 300 ppm to about 2 weight % of at least one hydrogenable contaminant, from 200 to about 5 weight % of at least one hydrogenable contaminant, or from about 200 ppm to about 4 weight % of at least one hydrogenable contaminant, or from about 200 ppm to about 3 weight % of at least one hydrogenable contaminant, or from about 200 ppm to about 2 weight % of at least one hydrogenable contaminant, or from 100 to about 5 weight % of at least one hydrogenable contaminant, or from about 100 ppm to about 4 weight % of at least one hydrogenable contaminant, or from about 100 ppm to about 3 weight % of at least one hydrogenable contaminant, or from about 100 ppm to about 2 weight % of at least one hydrogenable contaminant, or from 50 ppm to about 5 weight % of at least one hydrogenable contaminant, or from about 50 ppm to about 4 weight % of at least one hydrogenable contaminant, or from about 50 ppm to about 3 weight % of at least one hydrogenable contaminant, or from about 50 ppm to about 2 weight % of at least one hydrogenable contaminant. In accordance with the present invention, this product having at least one of the above ranges of hydrogenable contaminants is identified as the low purity or impure alcohol feed.

The impure alcohol feed containing at least one hydrogenable contaminant is contacted with a hydrogen containing gas under suitable conditions to saturate, i.e., hydrogenate the C=C and/or C=O bond(s) present in the hydrogenable contaminant and convert the hydrogenable contaminant into a hydrogenated contaminant. For example, in the case where the impure alcohol comprises ethylene glycol monobutyl ether, hydrogenable contaminants may comprise n-butyraldehyde, iso-butyraldehyde, 2-ethylhexenal, 2-ethylhexanal, 2-ethylhex-2-en-1-ol and mixtures thereof. The hydrogenation step would convert the hydrogenable contaminants into hydrogenated contaminant such as n-butanol, and 2-ethylhexanol to name a few.

In the hydrogenation process, it is common to use a reactor, which usually contains a solid hydrogenation catalyst having an active metal supported on a solid carrier such as diatomaceous earth, aluminum oxide, or celite. The hydrogenation catalyst employable herein is not specifically limited so far as it can catalyze the hydrogenation reaction of the hydrogenable contaminant(s). In practice, however, a catalyst containing a metal such as nickel, ruthenium, palladium and platinum, mixture of copper oxide and zinc oxide, a copper-chromium catalyst, copper-chromium-manganese-barium catalyst or the like may be used. Although not to be bound by any theory, it is believed that during hydrogenation at least one of the following reactions is/are occurring:

$$N\text{-butyraldehyde} + H_2 \rightarrow N\text{-butanol} \quad (1)$$

$$2\text{-ethylhexanal} + 2H_2 \rightarrow 2\text{-ethylhexanol} \quad (2)$$

$$2\text{-ethylhexanal} + H_2 \rightarrow 2\text{-ethylhex-2-en-1-ol} \quad (3)$$

$$2\text{-Ethylhex-2-en-1-ol} + H_2 \rightarrow 2\text{-ethylhexanol} \quad (4)$$

$$2\text{-butoxyethanol} + H_2 \rightarrow N\text{-butanol} + \text{ethanol} \quad (5)$$

$$2\text{-butoxyethanol} + H_2 \rightarrow 1\text{-ethoxy butane} + \text{water} \quad (6)$$

$$2\text{-butoxyethanol} + 2H_2 \rightarrow 1\text{-methoxy butane} + \text{methane} + \text{water} \quad (7)$$

Normal Impurities in Enal Hydrogenation $$2(2\text{-ethylhexanol}) + 2\text{-ethylhexanal} \rightarrow C_{24} \text{ Acetal} + \text{water} \quad (8)$$

$$2\text{-ethylhexanol} + 2\text{-ethylhexanal} + H2 \rightarrow C_{16} \text{ ether} + \text{water} \quad (9)$$

$$2(2\text{-ethylhexanol}) + N\text{-butyraldehyde} \rightarrow C_{12} \text{ Acetal} + \text{water} \quad (10)$$

The mode for carrying out the reaction may be in the vapor phase where the starting feed is vaporized or in the liquid phase where a starting feed is introduced as a liquid into a reactor. The reaction process may be either batch-wise or continuous. The catalyst can be suspended such as in a liquid reaction medium. Alternatively, the catalyst can be used in the form of molded bodies such as pellets, granulates, spheres, extruded blanks and arranged in a reactor as a fixed bed. This fixed-bed reactor can be operated in a flooded state as a bubble reactor or can be operated as a trickle-bed reactor.

In the hydrogenation reactor, hydrogenation of the contaminant is usually carried out under the reaction conditions of pressure of from atmospheric pressure to 200 kg/cm², or from atmospheric pressure to 100 kg/cm², or from atmospheric pressure to 10 kg/cm², and at a temperature of from about 20° C. to about 300° C., or from 50° C. to about 250° C., or from 50° C. to about 150° C. One skilled in the art will adapt the conditions of pressure and temperature to the catalyst, compounds to be hydrogenated as well as physical parameters of the hydrogenation reactor.

During hydrogenation, at least 10 mole percent of at least one hydrogenable contaminant in the impure alcohol is converted to a hydrogenated compound having at least one unsaturated bond becoming a saturated bond. It is part of the invention that at least 15 mole percent of at least one hydrogenable contaminant in the impure alcohol is converted to a hydrogenated compound having at least one unsaturated bond becoming a saturated bond, or at least 20 mole percent of at least one hydrogenable contaminant in the impure alcohol is converted to a hydrogenated compound having at least one unsaturated bond becoming a saturated bond, or at least 25 mole percent of at least one hydrogenable contaminant in the impure alcohol is converted to a hydrogenated compound having at least one unsaturated bond becoming a saturated bond, or at least 30 mole percent of at least one hydrogenable contaminant in the impure alcohol is converted to a hydrogenated compound having at least one unsaturated bond becoming a saturated bond, or at least 35 mole percent of at least one hydrogenable contaminant in the impure alcohol is converted to a hydrogenated compound having at least one unsaturated bond becoming a saturated bond, or at least 40 mole percent of at least one hydrogenable contaminant in the impure alcohol is converted to a hydrogenated compound having at least one unsaturated bond becoming a saturated bond, or at least 45 mole percent of at least one hydrogenable contaminant in the impure alcohol is converted to a hydrogenated compound having at least one unsaturated bond becoming a saturated bond, or at least 50 mole percent of at least one hydrogenable contaminant in the impure alcohol is converted to a hydrogenated compound having at least one unsaturated bond becoming a saturated bond, or at least 55 mole percent of at least one hydrogenable contaminant in the impure alcohol is converted to a hydrogenated compound having at least one unsaturated bond becoming a saturated bond, or at least 60 mole percent of at least one hydrogenable contaminant in the impure alcohol is converted to a hydrogenated compound having at least one unsaturated bond becoming a saturated bond, or at least 65 mole percent of at least one hydrogenable contaminant in the impure alcohol is converted to a hydrogenated compound having at least one unsaturated bond becoming a saturated bond, or at least 70 mole percent of at least one hydrogenable contaminant in the impure alcohol is converted to a hydrogenated compound having at least one unsaturated bond becoming a saturated bond, or at least 75 mole percent of at least one hydrogenable contaminant in the impure alcohol is converted to a hydrogenated compound having at least one unsaturated bond becoming a saturated bond, or at least 80 mole percent of at least one hydrogenable contaminant in the impure alcohol is converted to a hydrogenated compound having at least one unsaturated bond becoming a saturated bond, or at least 85 mole percent of at least one hydrogenable contaminant in the impure alcohol is converted to a hydrogenated compound having at least one unsaturated bond becoming a saturated bond, or at least 90 mole percent of at least one hydrogenable contaminant in the impure alcohol is converted to a hydrogenated compound having at least one unsaturated bond becoming a saturated bond, or at least 95 mole percent of at least one hydrogenable contaminant in the impure alcohol is converted to a hydrogenated compound having at least one unsaturated bond becoming a saturated bond, or at least 99 mole percent of at least one hydrogenable contaminant in the impure alcohol is converted to a hydrogenated compound having at least one unsaturated bond becoming a saturated bond.

In accordance with the present invention, the method includes the step of separating the low purity or impure alcohol from the hydrogenated contaminant to produce an alcohol product having a higher purity relative to the low purity alcohol feed. Separation and purification to individual alcohols may be by any known method such as distillation and flash evaporation and optionally separation is performed under an oxygen free atmosphere. As by-products to be separated, there are high-boiling components such as esters, acetals, and ethers formed by esterification, acetalization, etherification, and the like that are side reactions at the hydrogenation reaction, and low-boiling components such as decomposed products thereof, unreacted aldehyde, and isomer alcohols. The hydrogenated contaminants and the product alcohol have greatly different boiling points and thus can be easily separated from each other. For example, the boiling point of n-butyl alcohol is 117.7° C., and 2-ethylhexanol is 183.5° C. while EB has a boiling point of 171.32° C.

In the invention, the distillation is not particularly limited but is usually carried out under atmospheric pressure or reduced pressure, preferably under reduced pressure. The preference is for the purpose of decreasing heat load at the bottom of the distillation column and also lowering the temperature level of the reboiler heat source. Specifically, it is preferred to run the distillation under the condition of a bottom temperature of 150° C. or lower.

In the invention, distillation is not limited and may include a distillation column optionally having a reflux drum, a condenser, a reboiler, and/or a preheater. Of course, the distillation column may have other ancillary pieces of equipment known to those skilled in the art as according to the need. Additionally, the number of theoretical stages of separation in the distillation column may be suitably determined and varied if needed.

Moreover, the separation step may include a plurality of steps such as using a 2-column, 3-column or 4-column mode. This contemplates a method wherein high-boiling impurities, such as esters and acetals are removed in the first column to prevent their subsequent decomposition and generation of new low-boiling impurities later in the process. Then the product alcohol was distilled in the second column to remove the low boiling impurities. The product alcohol, which is removed as a bottom product from the second column, may be sent to a third, flash column to remove color bodies and/or trace metals and salts, or alternatively may be removed as a vapor side draw near the bottom of the second column. Additional columns may be added to recover product alcohol from the first column bottoms and/or the second column overhead for recycle and recovery. By whatever means the separation is carried out, it has been advantageously discovered that hydrogenating the hydrogenable contaminants, and particularly the non ethylene glycol monoether contaminants, and separating the hydrogenated contaminants from the ethylene glycol monoether it is possible to obtain a higher purity alcohol such as a higher purity ethylene glycol monobutyl ether, relative to the low purity feed.

In accordance with the present invention, the higher purity or enriched alcohol product has substantially less hydrogenable contaminants relative to the impure alcohol feed. For example, the impure alcohol composition comprises enols and the concentration of the enols in the enriched alcohol composition is reduced by at least 50 mole % relative to the concentration of all enols in the impure alcohol composition. The invention also include the case where the enols in the enriched alcohol composition is reduced by at least 60 mole % relative to the concentration of all enols in the impure alcohol composition, or enols in the enriched alcohol composition is reduced by at least 70 mole % relative to the concentration of all enols in the impure alcohol composition, or enols in the enriched alcohol composition is reduced by at least 80 mole % relative to the concentration of all enols in the impure alcohol composition, or enols in the enriched alcohol composition is reduced by at least 90 mole % relative to the concentration of all enols in the impure alcohol composition, or enols in the enriched alcohol composition is reduced by at least 95 mole % relative to the concentration of all enols in the impure alcohol composition, or enols in the enriched alcohol composition is reduced by at least 99 mole % relative to the concentration of all enols in the impure alcohol composition.

The enriched alcohol composition comprises enals and the concentration of enals in the enriched alcohol composition can be reduced by at least 50 mole % relative to the concentration of all enals in the impure alcohol composition, or the enals in the enriched alcohol composition is reduced by at least 60 mole % relative to the concentration of all enals in the impure alcohol composition, or enals in the enriched alcohol composition is reduced by at least 70 mole % relative to the concentration of all enals in the impure alcohol composition, or enals in the enriched alcohol composition is reduced by at least 80 mole % relative to the concentration of all enals in the impure alcohol composition, or enals in the enriched alcohol composition is reduced by at least 90 mole % relative to the concentration of all enals in the impure alcohol composition, or enals in the enriched alcohol composition is reduced by at least 95 mole % relative to the concentration of all enals in the impure alcohol composition, or enals in the enriched alcohol composition is reduced by at least 99 mole % relative to the concentration of all enals in the impure alcohol composition.

The impure alcohol composition comprises alkylene glycols, and the concentration of the alkylene glycols in the enriched alcohol composition has an absolute value difference of at least 10 weight percent relative to the concentration of all alkylene glycols in the impure alcohol composition, or the concentration of the alkylene glycols in the purified alcohol composition has an absolute value difference of at least 25 weight percent relative to the concentration of all alkylene glycols in the impure alcohol composition, or the concentration of the alkylene glycols in the purified alcohol composition has an absolute value difference of at least 50 weight percent relative to the concentration of all alkylene glycols in the impure alcohol composition, or the concentration of the alkylene glycols in the purified alcohol composition has an absolute value difference of at least 75 weight percent relative to the concentration of all alkylene glycols in the impure alcohol composition.

It is further understood that the impure alcohol composition comprises water, and the concentration of the water in the enriched alcohol composition has a difference value of at least 10 ppm relative to the concentration of water in the impure alcohol composition, or the concentration of the water in the enriched alcohol composition has a difference value of at least 50 ppm relative to the concentration of water in the impure alcohol composition, or the concentration of the water in the enriched alcohol composition has a difference value of at least 100 ppm relative to the concentration of water in the impure alcohol composition.

Advantageously, in accordance with the present invention the impure alcohol composition comprises at least one alcohol ether compound having a first weight percent, based on the weight of the impure alcohol composition, and the purified alcohol composition has a second weight percent of the alcohol ether compound, based on the weight of the purified alcohol composition, and the second weight percent of the alcohol ether compound is larger than the first weight percent with an absolute value of their difference ranging from 0.15 to 0.5; or the second weight percent of the alcohol ether compound is larger than the first weight percent with an absolute value of their difference ranging from 0.2 to 0.5; or the second weight percent of the alcohol ether compound is larger than the first weight percent with an absolute value of their difference ranging from 0.25 to 0.5.

As noted above, after separation is carried out, it has been advantageously discovered that it is possible to obtain an alcohol composition having an enriched concentration of the desired alcohol and significantly lower concentrations of contaminants. Accordingly, an alcohol composition can be selected from alcohols that are the reaction product from a primary alcohol reactant and an ethylene oxide reactant wherein the alcohol composition comprises less than about 500 ppm of at least one hydrogenable contaminant comprising an aldehyde, an enal, an enol, and mixtures thereof.

When the primary alcohol reactant comprises methanol, ethanol, and n-butanol. The reaction product is primarily a glycol monoether selected from ethylene glycol monomethyl ether, ethylene glycol monoethyl ether, ethylene glycol monobutyl ether and mixtures thereof and includes at least one hydrogenable contaminant comprising n-butryaldehyde, iso-butyraldehyde, 2-ethylhexenal, 2-ethylhex-2-en-1-ol, and mixtures thereof. Accordingly, utilizing the process of the present invention it is possible to obtain an alcohol composition comprising less than about 200 ppm of at least one hydrogenable contaminant comprising an aldehyde, an enal, an enol, and mixtures thereof, or an alcohol composition comprising less than about 150 ppm of at least one hydrogenable contaminant comprising an aldehyde, an enal, an enol, and mixtures thereof, or an alcohol composition comprising less than about 50 ppm of at least one hydrogenable contaminant comprising an aldehyde, an enal, an enol, and mixtures thereof.

The present invention is illustrated in greater detail by the specific examples presented below. It is to be understood that these examples are illustrative purposes and are not intended to be limiting of the invention, but rather are to be construed broadly within the scope and content of the appended claims. All parts and percentages in the examples are on a mass basis unless otherwise stated.

Example 1

A low purity alcohol feed, ethylene glycol monobutyl ether feed (99.6 wt %), containing 220 ppm 2-ethylhexenal and 722 ppm 2-ethylhex-2-en-1-ol (enol) was fed to a reactor top at a flow rate of 10 g/min. The reactor was a fixed-bed reactor, 1" (inside diameter)×72" (height), charged with 600 ml of a Nickel catalyst. The reactor was operated at a temperature of from 80° C. to 130° C. and top pressure of 240 to about 250 psig. The reactor ran continuously. Hydrogen and reactor feed were fed to the reactor top. The reactor exit was at the bottom. After a vapor/liquid separation to remove the excess hydrogen, the bottom product was recycled back to the reactor top at a flow rate of about 100 g/min. The reactor product contained 4 ppm 2-ethylhexenal and no detectable amount of 2-ethylhex-2-en-1-ol. Detection was determined by gas chromatography. The hydrogenated reactor product was composed of 99.45% EB, 1100 ppm 2-ethylhexanol, and 1500 ppm of n-butanol with 2-ethylhexenal and enol below the detection limit. The hydrogenated product also contains 183 ppm ethylene glycol and 385 ppm 2-isobutoxyethanol which were the compounds originally carried in by the feed. The feed composition is more completely described in Table 1.

Example 2

The same reactor as in Example 1 was charged with 600 ml of a Ruthenium catalyst. A low purity alcohol feed ethylene glycol monobutyl ether feed (99.6 wt %), containing 280 ppm 2-ethylhexenal and 960 ppm 2-ethylhex-2-en-1-ol was fed to the reactor as described in Example 1 above at a flow rate of 6 g/min and reactor recycle flow rate of 60 g/min. The reactor was operated at a temperature of from 30° C. to about 90° C. and pressure of from 240 to about 250 psig. The reactor product contained no detectable amount of 2-ethylhexenal and 2-ethylhex-2-en-1-ol. The hydrogenated EB product contained 99.0% EB, and 2200 ppm 2-ethylhexanol 400 ppm butanol and 2-ethylhexenal and enol below the detection limit. The hydrogenated product also contains ethylene glycol and 2-isobutoxyethanol which were the compounds originally carried in by the feed.

Example 3

Example 2 was repeated but at feed rate of 20 g/min and recycle flow rate of 100 g/min. The reactor was controlled at a hydrogen partial pressure of 400 psig. The reactor product contained no detectable amount of 2-ethylhexenal and 2-ethylhex-2-en-1-ol.

Example 4

A collective liquid hydrogenation reactor product was fed to two—2 inch diameter glass Oldershaw columns. Each column had a total of 35 trays. The feed to the first column was preheated to 110° C. and introduced on the 10th tray from the bottom. The feed rate was 6.3 g/min. The base temperature was set at 175° C. and was controlled by adjusting the power input (Variable Autotransformer by Staco Inc.) to a heating mantle that surrounded a three port 2000 mL glass round bottom flask. The flask was purged intermittently through a liquid dip tube to remove the heavies including 2-ethylhexanol (0.3 g/min) to keep the liquid level relatively constant at 1000 mL. The vapor from the top of first column was condensed by a cooling water condenser. The condensed liquid was either refluxed back to the first column or sent to the second column. A Therm-O-Watch temperature control, available from Glas Col, LLC, was used to set the reflux ratio to hold the top of the first column temperature at 170° C., generally around 3-10. A positive nitrogen blanket was kept on the first column to exclude air using a gas bubbler fabricated in house.

The overhead from the first column was preheated to 130° C. and introduced on the 25$^{th}$ tray from the bottom of the second column. The feed rate was 6.0 g/min. The base temperature of the second column was set at 170° C. and was controlled by a heating mantle around a flask as described above. The purified EB was removed from the vapor space in the second flask at a rate of 5.88 g/min and then condensed (cooling water) and sent to a product collection tank. The vapor from the top of the second column is condensed by cooling water and returned to the second column as reflux or removed from the distillation train. A Therm-O-Watch temperature control was used to set the reflux ratio near total reflux to hold the second column top temperature around 162° C. The overhead stream, about 0.12 g/min containing the lights such as normal butanol was collected and then disposed of A positive nitrogen blanket was kept on the second column and product tank using a gas bubbler. The final product contains 99.9 weight percet 2-butoxyethanol, 17 ppm n-butanol, 340 ppm ethylene glycol, 196 ppm 2-isobutoxyethanol, 144 ppm 2-ethylhexanol and no metals (Aluminum, Antimony, Arsenic, Barium, Boron, Cadmium, Calcium, Chromium, Cobalt, Copper, Gallium, Germanium, Iron, Lead, Lithium, Magnesium, Manganese, Molybdenum, Nickel, Potassium, Silver, Sodium, Strontium, Tin, Titanium, and Zinc) above 25 ppb were detected. The product composition is more completely described in Table 1 below.

TABLE 1

| Compound | Feed Conc. | Hydrogen Rx Exit | Final Product |
|---|---|---|---|
| N-butyraldehyde | 77 ppm | Below detection | 28 ppm |
| N-Butanol | 43 ppm | 1553 ppm | 17 ppm |
| 2-ethylhexanal | 0 | | |
| n-butyl ether | 0 | | |
| 2-ethylhexenal | 220 ppm | 4 ppm | Below detection |
| 2-isobutoxyethanol | 722 ppm | 385 ppm | 196 ppm |
| 2-butoxyethanol | 99.64 wt. % | 99.4 wt. % | 99.92 wt. % |
| 2-ethylhexanol | 168.5 ppm | 1166 ppm | 144 ppm |
| DEG-m-E-ether | 252 ppm | 170 ppm | |
| 2-Ethylhex-2-en-1-ol | 692 ppm | 0 | Below detection |
| ethylene glycol | 187 ppm | 183 ppm | 340 ppm |
| Unknowns/others | 285.2 ppm | 800 ppm | 121 ppm |
| Water | 0 | 1800 ppm | 60 ppm |

Having described the invention in detail, those skilled in the art will appreciate that modifications may be made to the various examples of the invention without departing from the scope and spirit of the invention disclosed and described herein. Therefore, it is not intended that the scope of the invention be limited to the specific examples illustrated and described but rather it is intended that the scope of the present invention be determined by the appended claims and their equivalents.

What is claimed is:

1. A method for making a higher purity alcohol comprising:
   a. contacting an impure alcohol composition comprising:
      (i) ethylene glycol monobutyl ether; and
      (ii) from about 50 ppm to about 5 weight percent, based on the weight of the impure alcohol composition, of at least one hydrogenable contaminant having an unsaturated bond comprising n-butyraldehyde, isobutyraldehyde, 2-ethylhexenal, 2-ethylhexanal, 2-ethylhex-2-en-1-ol and mixtures thereof, and
      (iii) water,
   with hydrogen in a hydrogenation reactor and in the presence of a hydrogenation catalyst to produce a reaction mixture comprising said ethylene glycol monobutyl ether and a hydrogenated contaminant product and wherein at least 50 mole % of at least one said hydrogenable contaminant in said reaction mixture is converted; and
   b. separating ethylene glycol monobutyl ether from at least a portion of said reaction mixture to produce a purified alcohol composition having a concentration of said hydrogenable contaminant that is lower than the concentration of said hydrogenable contaminant in said impure alcohol composition and wherein the ethylene glycol monobutyl ether in the purified alcohol composition has an absolute difference of at least 10 weight percent relative to the concentration of ethylene glycol monobutyl ether in the impure alcohol composition.

2. The process of claim 1 wherein at least 60 mole % of said at least one hydrogenable contaminant in said reaction mixture is converted.

3. The process of claim 1 wherein at least 80 mole % of said at least one hydrogenable contaminant in said reaction mixture is converted.

4. The process of claim 1 wherein at least 95 mole % of said at least one hydrogenable contaminant in said reaction mixture is converted.

5. The process of claim 1 wherein the impure alcohol composition comprises enols and the concentration of the enols in the purified alcohol composition is reduced by at least 90 mole % relative to the concentration of all enols in the impure alcohol composition.

6. The process of claim 5 wherein the concentration of the enols in the purified alcohol composition is reduced by at least 95 mole % relative to the concentration of all enols in the impure alcohol composition.

7. The process of claim 5 wherein the concentration of the enols in the purified alcohol composition is reduced by at least 99 mole % relative to the concentration of all enols in the impure alcohol composition.

8. The process of claim 1 wherein the impure alcohol composition comprises enals and the concentration of the enals in the purified alcohol composition is reduced by at least 90 mole % relative to the concentration of all enals in the impure alcohol composition.

9. The process of claim 8 wherein the concentration of the enals in the purified alcohol composition is reduced by at least 95 mole % relative to the concentration of all enals in the impure alcohol composition.

10. The process of claim 8 wherein the concentration of the enals in the purified alcohol composition is reduced by at least 99 mole % relative to the concentration of all enals in the impure alcohol composition.

11. The process of claim 1 wherein the concentration of ethylene glycol monobutyl ether in the purified alcohol composition has an absolute difference of at least 25 weight percent relative to the concentration of ethylene glycol monobutyl ether in the impure alcohol composition.

12. The process of claim 11 wherein the concentration of ethylene glycol monobutyl ether in the purified alcohol composition has an absolute difference of at least 50 percent relative to the concentration of ethylene glycol monobutyl ether in the impure alcohol composition.

13. The process of claim 12 wherein the concentration of ethylene glycol monobutyl ether in the purified alcohol composition has an absolute difference of at least 75 percent relative to the concentration of all ethylene glycol monobutyl ether in the impure alcohol composition.

14. The process of claim 1 wherein the concentration of the water in the purified alcohol composition has a difference of at least 10 ppm relative to the concentration of water in the impure alcohol composition.

15. The process of claim 1 wherein the concentration of the water in the purified alcohol composition has a difference of at least 50 ppm relative to the concentration of water in the impure alcohol composition.

16. The process of claim 1 wherein the concentration of the water in the purified alcohol composition has a difference of at least 100 ppm relative to the concentration of water in the impure alcohol composition.

17. The process of claim 1 wherein the impure alcohol composition comprises ethylene glycol monobutyl ether at a first weight percent based on the weight of the impure alcohol composition, and the purified alcohol composition has said ethylene glycol monobutyl ether at a second weight percent based on the weight of the purified alcohol composition, wherein the second weight percent is larger than the first weight percent and the absolute value of their difference ranges from 0.15 to 0.5.

18. The process of claim 17 wherein the second weight percent of the ethylene glycol monobutyl ether is larger than the first weight percent and the absolute value of their difference is from 0.2 to 0.5.

19. The process of claim 17 wherein the second weight percent of the ethylene glycol monobutyl ether is larger than the first weight percent and the absolute value of their difference is from 0.25 to 0.5.

20. The method of claim 1 wherein said separating step comprises distilling said reaction mixture.

* * * * *